United States Patent [19]

Sumiya et al.

[11] Patent Number: 5,668,078
[45] Date of Patent: Sep. 16, 1997

[54] WATER-ABSORBENT RESIN PARTICLES AND THE PRODUCTION THEREOF

[75] Inventors: Takashi Sumiya, Shiga-ken; Masanori Koike, Kyoto-fu; Kenji Tanaka, Shiga-ken, all of Japan

[73] Assignee: Sanyo Chemical Industries, Ltd., Kyoto-fu, Japan

[21] Appl. No.: 476,718

[22] Filed: Jun. 7, 1995

[30] Foreign Application Priority Data

Oct. 5, 1994 [JP] Japan ................................ 6-268283

[51] Int. Cl.$^6$ .................................................. B01J 20/26
[52] U.S. Cl. ...................................... 502/402; 502/407
[58] Field of Search ................................. 502/402, 407

[56] References Cited

U.S. PATENT DOCUMENTS

| | | | |
|---|---|---|---|
| 4,755,560 | 7/1988 | Ito et al. | 525/100 |
| 5,075,373 | 12/1991 | Takemori et al. | 525/57 |

FOREIGN PATENT DOCUMENTS

| | | | |
|---|---|---|---|
| 0 195 406 | 9/1986 | European Pat. Off. | C08F 8/42 |
| 0 415 183 | 3/1991 | European Pat. Off. | A61L 15/22 |
| 56-133028 | 10/1981 | Japan . | |
| 59-080459 | 5/1984 | Japan . | |
| 61-069854 | 4/1986 | Japan . | |
| 61-264006 | 11/1986 | Japan . | |
| 63-105064 | 5/1988 | Japan . | |
| 5-70625 | 3/1993 | Japan . | |

OTHER PUBLICATIONS

Abstract from *Derwent Publications Ltd.*, JP-63-108031, dated 12 May 1988.

Abstract from *Derwent Publications Ltd.*, JP-57-0061775 dated 14 Apr. 1982.

Abstract from *Derwent Publications Ltd.*, JP-63-028977 dated 6 Feb. 1988.

Copy of European Search Report dated Jan. 16, 1996.

*Primary Examiner*—Glenn A. Caldarola
*Assistant Examiner*—In Suk Bullock

[57] ABSTRACT

The present invention relates to a process for producing improved water-absorbent resin particles comprising the step of treating water-absorbent particles, which are crosslinked polymers of ethylenically unsaturated monomers comprising acrylic acid and/or acrylic acid salt as an essential element, with a modified silicone oil having a functional group which can react with a carboxyl group and/or a carboxylate group in the molecule Improved water-absorbent resin particles obtained by the process have a hygroscopic blocking rate of 20 % or less under a relative humidity of 80 % at 40° C., a dust level of 10 CPM or less and an absorbing characteristic of initial absorbency under load to physiological saline of 20 times or more. The present invention provides water-absorbent resin particles which have an improved hygroscopic blocking rate under high humidity and dust generation rate with a good initial absorbency under load and absorbing capacity.

12 Claims, No Drawings

WATER-ABSORBENT RESIN PARTICLES AND THE PRODUCTION THEREOF

BACKGROUND OF THE INVENTION

1. Field of the Invention

The present invention relates to improved water-absorbent resin particles and the production thereof. More specifically, it relates to a process for producing water-absorbent resin particles comprising the step of treating water-absorbent resin particles with a certain kind of-a modified silicone oil, and to water-absorbent resin particles obtained by the process having a low hygroscopic blocking rate and dust level, and a good initial absorbency under load.

2. Description of the Prior Art

Conventional water-absorbent resins are broadly used in hygienic materials such as sanitary materials, disposable diapers or water retaining materials for soil. Examples of such water-absorbent resins include substantially water-insoluble water-absorbing crosslinked polymers such as crosslinked polyacrylic acid salts, self-crosslinked polyacrylic acid salts, crosslinked graft-copolymers of starch-acrylic acid salts, crosslinked copolymers of vinyl alcohol-acrylic acid salts, hydrolyzed crosslinked copolymers of acrylamide, neutralized crosslinked copolymers of isobutylene-maleic acid anhydride, and crosslinked carboxymethyl cellulose salts.

Although such water-absorbent resins can absorb a great amount of water or urine, the absorbing capability causes problems such as blocking of the water-absorbing resin particles by absorbing moisture, adhesion to the machine, or disabling the discharge of water-absorbing resin particles from the hopper or continuous regular supply to the machine in the process of storing or providing the water-absorbing resin particles to the machine for producing disposable diapers in conditions of high humidity.

As the means to improve the hygroscopic blocking rate, methods as the following examples ①-④ have been proposed:

① a method of mixing hydrophobic silica fine particles having an average particle size of 0.05 μm or smaller and a specific surface area of 50 m²/ g or greater to the water-absorbing resin particles as disclosed in the Japanese Patent Application Laid Open No. 133028/1981.

② a method of adding inorganic particles such as hydrated silicon dioxide, hydrated aluminum hydroxide, hydrated titanium hydroxide to the water-absorbing resin particles as disclosed in the Japanese Patent Application Laid Open No. 80459/1984.

③ a method of treating the water-absorbent resin particles with a cationic surface active agent and further adding organic compound particles having a high melting point as disclosed in the Japanese Patent Application Laid Open No. 69854/1986.

④ a method of mixing stearic acid and inorganic powders to the water-absorbing resin particles to form a film of stearic acid on the surface of the water-absorbing resin particles as disclosed in the Japanese Patent Application Laid Open No. 105064/1988.

Although the method ① of adding a hydrophobic silica contributes to improving the hygroscopic blocking rate, it has problems such as reducing the initial absorbency under load and absorbing capacity due to the surface of the water-absorbing resin particles being covered with the hydrophobic silica, or generating much dust due to the mixed fine powders of silica. When the inorganic powders of the method ② are not hydrophobic, although it does not reduce the initial absorbency under load or absorbing capacity, it has problems such as insufficient improvement of the hygroscopic blocking rate, generating much dust due to the mixed fine powders of inorganic silica like the method ①. The methods ③ and ④ of covering the surface of the water-absorbing resin particles with a hydrophobic organic compound having a high melting point or stearic acid improve the hygroscopic blocking rate to some extent but not sufficiently. Besides, they have problems such as reducing the initial absorbency under load and the absorbing capacity due to the organic compound having a high melting point or the stearic acid hindering the absorbing ability of the water-absorbing resins.

SUMMARY OF THE INVENTION

The present inventors earnestly studied the means to solve the above-mentioned problems of the methods ①-④ for improvement and worked out the process of producing water-absorbent resin particles by treating substantially water-insoluble water-absorbent resin particles, which are crosslinked polymers of ethylenically unsaturated monomers comprising acrylic acid and/or acrylic acid salt as an essential element, with a modified silicone oil having a functional group in its molecules which can react with a carboxyl group and/or a carboxylate group. This fixes the silicone oil on the surface of the water-absorbing resin particles to improve the hygroscopic blocking rate in high humidity and reduce the generation of dust by providing wettability, and further improves the initial absorbency under load and absorbing capacity by reacting the functional group of the modified silicone oil with a carboxyl group and/or a carboxylate group of the water-absorbent resin particles. The improved water-absorbing resin particles obtained by this method have been found to have a low hygroscopic blocking rate in high humidity and a low dust level and a good initial absorbency under load and absorbing capacity.

It is an object of the present invention to provide water-absorbent resin particles having an improved hygroscopic blocking rate and a dust level with a good initial absorbency under load and an absorbing capacity, and a production process thereof.

That is, the present invention provides a production process for improved water-absorbent resin particles comprising the step of treating substantially water-insoluble water-absorbent resin particles, which are crosslinked polymers of an ethylenically unsaturated monomers comprising acrylic acid and/or acrylic acid salt as an essential element, with a modified silicone oil having a functional group which can react with a carboxyl group and/or a carboxylate group in its molecules; and also provides improved water-absorbent resin particles which have a hygroscopic blocking rate of 20% or less in the relative humidity of 80% at 40° C., a dust level of 10 CPM or less, and absorbing characteristics of an initial absorbency under load of 20 times or more to physiological saline.

Water-absorbent resin particles used as an ingredient in the present invention are substantially water-insoluble water-absorbent resin particles which absorb considerable amounts of water when in contact with water to swell and form a hydrogel. Any crosslinked polymer of ethylenically unsaturated monomers comprising acrylic acid and/or acrylic acid salt as an essential element can be used as such water-absorbent resins. Examples of such crosslinked polymers include at least one resin selected from the group consisting of crosslinked partially neutralized polyacrylic acid, self-crosslinked partially neutralized polyacrylic acid, crosslinked graft-copolymers of starch-acrylic acid salt, hydrolyzed crosslinked graft-polymers of starch-acrylonitrile, crosslinked copolymers of vinyl alcohol-acrylic acid salt, crosslinked copolymers of acrylic acid-acrylamide, hydrolyzed crosslinked copolymers of acrylic acid salt-acrylonitrile, crosslinked copolymers of acrylic acid salt and 2-acrylamide-2-methyl propane sulfonate, neutralized crosslinked copolymers of isobutylene-maleic anhydride. Examples of the above-mentioned salts include sodium salt, potassium salt, ammonium salt and amine salt.

Among the above examples, crosslinked partially neutralized polyacrylic acid, self-crosslinked partially neutralized polyacrylic acid, crosslinked graft-copolymers of starch-acrylic acid salt and crosslinked copolymers of vinyl alcohol-acrylic acid salt are preferable in consideration of the absorbing characteristics of the water-absorbent resins finally obtained. Moreover, water-absorbent resin particles obtained by further crosslinking the vicinity of the surface of the above-mentioned water-absorbent resin particles can be used preferably as the ingredient in this invention. An example of the crosslinking the vicinity of the surface of the water-absorbent resin particles is disclosed in the U.S. Pat. No. 5,322,896.

The shape of the water-absorbent resin particles used as the ingredient is not particularly limited. Therefore, any shape obtained from the production process, such as spherical shape obtained in reversed phase suspension polymerization, lamellar shape obtained in drum drying, block shape or random shape obtained in pulverizing a resin lump and agglomerates of such particles, can be used. Besides, the size of the particle is not particularly limited, but in general, from 10 to 1,000 μm, preferably from 100 to 850 μm and in general, the average particle size is from 200 to 600 μm.

The modified silicone oil used in the present invention has at least one functional group which can react with a carboxyl group and/or a carboxylate group. A "carboxylate group" herein denotes a carboxylic acid salt group. Concrete examples of such modified silicone oil include amino modified silicone oil, epoxy modified silicone oil, carbinol modified silicone oil, phenol modified silicone oil and mercapto modified silicone oil. Among these examples, since amino modified silicone oil and epoxy modified silicone oil react with water-absorbent resin particles at a relatively low temperature, they are preferable.

Examples of the amino modified silicone oil include a silicone oil which has a group illustrated as —$R^1NR^2R^3$ at an end of the silicone polymer molecules and/or in the molecules. (Herein $R^1$ denotes an alkylene group of 1 to 12 carbon atoms; $R^2$, $R^3$ denote H or an alkyl group of 1 to 12 carbon atoms. One or more hydrogen atoms in the alkylene group and/or alkyl group can be replaced by a hydroxyl group, a carboxyl group or an amino group. When the number of the carbon atoms is two or more, an ether linkage having an oxygen atom between carbon-carbon bonds can be included.)

Examples of the epoxy modified silicone oil include a silicone oil which has a group illustrated as —RX at an end of the silicone polymer molecules and/or in the molecules. (Herein R denotes an alkylene group of 1 to 12 carbon atoms; X denotes an epoxy group. One or more hydrogen atoms in the alkylene group can be replaced by a hydroxy group or carboxyl group. When the number of the carbon atoms is two or more, an ether linkage having an oxygen atom between carbon-carbon bonds can be included.)

In general, the number of the functional groups which can react with a carboxyl group and/or a carboxylate group can be one or more per molecule of the modified silicone oil, preferably two or more in order to crosslink the vicinity of the surface of the water-absorbent resin particles, and more preferably from 2 to 20 for the efficient crosslinking. It is not preferable to use an ordinary silicone oil not having a functional group which can react with a carboxyl group and/or a carboxylate group in its molecules since the silicone oil separates from the water-absorbent resin particles when absorbing moisture to have an insufficiently improved hygroscopic blocking rate, and the silicone oil adhered to the surface of the water-absorbent resin particles may prevent the initial absorption. The modified silicone oil can have a functional group at an end, at a side chain, or at both an end and a side chain.

The molecular weight of the modified silicone oil in this invention is not particularly limited, but in general is 1,000 or more, preferably 3,000 or more. If the molecular weight of a modified silicone oil is less than 1,000, the hygroscopic blocking rate or the dust level may deteriorate progressively. The viscosity of the modified silicone oil is not particularly limited, but preferably is from 10 to 20,000 centistokes (cst) at an ordinary temperature (25° C.). The maximum molecular weight of the silicone oil is not particularly limited, but in general is approximately 1,000,000.

The amount of modified silicone oil to water-absorbent resin particles in the present invention can vary, but in general, the weight ratio of (water-absorbent resin particles: modified silicone oil) is (100:0.001–5), preferably (100:0.01–3.0), more preferably (100:0.05–1.0). It is preferable to use a modified silicone oil in the above-mentioned range since it accomplishes a sufficiently improved hygroscopic blocking rate without liability of the deterioration of particle fluidity caused by the stickiness of the water-absorbent resin particles.

At the time of treating the water-absorbent resin particles with the modified silicone oil in the present invention, a further crosslinking agent having two or more functional groups which can react with a carboxyl group and/or a carboxylate group of the water-absorbent resin particles can be used as needed. Since the degree of crosslinking in the surface layer of the water-absorbent resin particles becomes denser by using a further crosslinking agent, the hygroscopic blocking rate can be further improved, and the absorbency under load can be improved as well. The kind of such crosslinking agents can vary depending upon the kind and the number of the functional groups in the modified silicone oil used. Examples of the crosslinking agent include polyglycidyl ether compounds, haloepoxy compounds, polyaldehyde compounds, polyhydric alcohol compounds and polyamine compounds.

Concrete examples of polyglycidyl ether compounds include ethylene glycol diglycidyl ether, propylene glycol diglycidyl ether, glycerol-1,3-diglycidyl ether, glycerol triglycidyl ether, polyethylene glycol diglycidyl ether and 1,6-hexanediol diglycidyl ether.

Concrete examples of haloepoxy compounds include epichlorohydrin and α-methyl epichlorohydrin.

Concrete examples of polyaldehyde compounds include glutaraldehyde and glyoxal.

Concrete examples of polyhydric alcohol compounds include glycerol, ethylene glycol, diethylene glycol, propylene glycol, polyethylene glycol, polypropylene glycol, diethanol amine and triethanol amine.

Concrete examples of polyamine compounds include ethylene diamine, diethylene triamine, triethylene tetramine, tetraethylene pentamine, polyamide resin as a reactant of polyamine and aliphatic acid, polyamine epichlorohydrin resin and polyamide polyamine epichlorohydrin resin.

Among the examples of the crosslinking agents, polyglycidyl ether compounds, polyhydric alcohol compounds and polyamine compounds are preferable. Among the preferable examples, ethylene glycol diglycidyl ether, propylene glycol diglycidyl ether, glycerol-1,3-diglycidyl ether, glycerol triglycidyl ether, polyamine epichlorohydrin resin, polyamide polyamine epichlorohydrin resin are more preferable since such compounds have a low reaction temperature and thus they are economical in terms of energy cost.

The amount of the crosslinking agent used in the present invention can vary depending upon the kind of the crosslinking agent, the kind and the crosslinking degree of the water-absorbent resin, the desired performance the improved water-absorbent resins is to obtain, but in general, the weight ratio of (water-absorbent resin: crosslinking agent) is (100:0.01– 5), preferably (100:0.05–3), more preferably (100:0.1–2). It is preferable to have a crosslinking agent in the above-mentioned range since it accomplishes the effect of adding the crosslinking agent sufficiently without the problem of the deterioration of the absorption caused by the excessively dense crosslinking degree.

The method of adding a modified silicone oil (and crosslinking agent optionally used) can be any method to add a prescribed amount of a modified silicone oil. Examples of such methods include a method of blending water-absorbent resin particles and a modified silicone oil (and a crosslinking agent) directly, a method of adding an emulsion of a silicone oil to water-absorbent resin particles and blending, a method of dispersing or dissolving a modified silicone oil (and a crosslinking agent) in a hydrophobic organic solvent and/or a hydrophilic organic solvent and then adding to water-absorbent resin particles and blending, and a method of dissolving or dispersing a modified silicone oil (and a crosslinking agent) in a solvent mixture comprising water and a hydrophilic organic solvent such as alcohol and adding to water-absorbent resin particles and blending.

As the device used in treating water-absorbent resin particles with a modified silicone oil (and a crosslinking agent), an ordinary blender such as a cylindrical blender, a screw blender, a screw extruder, a turbulizer, a Nauta blender, V-shaped rotating mixer, a ribbon blender, a double arm type kneader, a fluidized bed mixer, an air blender, a rotating disc type mixer and a roll mixer can be used.

A mixture obtained by the above-mentioned process can be heated to promote the reaction if necessary, depending on the reactivity of the functional groups in the modified silicone oil (and the crosslinking agent). The blending and heating can be conducted at the same time. The "reaction" herein denotes a crosslinking reaction between the water-absorbent resin particles and the modified silicone oil (and the crosslinking agent). The temperature of the optional heating is in general, 60° to 200° C., preferably 80° to 180° C. For the heating treatment, a drier or a heater such as a hot-air drier, a rotary drier, a paddle drier, a rotating disc drier, a fluidized bed drier, a belt type drier, a Nauta type drier and an infrared drier can be used.

The improved water-absorbent resin particles obtained in the above-mentioned method of the present invention are resin particles substantially water-insoluble, and for which the hygroscopic blocking rate, dust level and absorbing characteristics can be controlled according to the intended application thereof. The hygroscopic blocking rate in high humidity (of 40° C., 80% RH, after three hours) is in general, 20% or less, preferably 10% or less. The dust level of the water-absorbent resin particles is in general, 10 CPM or less, preferably 5 CPM or less. The initial absorbency under load to physiological saline is 20 times or more, preferably 25 times or more. Physiological saline herein denotes an aqueous solution of sodium chloride having a concentration of from 0.85 to 0.95 weight percent. Since the water-absorbent resin particles of the present invention do not cause hygroscopic blocking under high humidity nor generate dust in the production process of disposable diapers, etc. and have a good initial absorbency under load, when applied in a disposable diaper, etc., a good dry and smooth feeling after absorbing water, that is, a good feeling in the surface of the disposable diaper after absorbing urine, can be provided.

To the improved water-absorbent resin particles of the present invention, an antiseptic agent, a fungistat, a disinfectant, an antioxidant, a ultraviolet-absorber, a coloring agent, a perfume, a deodorant can be added at an optional stage.

The present invention will be further illustrated referring to examples and comparative examples, but the present invention is not limited only to them. The hygroscopic blocking rate, the dust level, the initial absorbency under load and the absorbing capacity are measured by the method described below. Hereinafter "%" refers to "weight %" unless specifically noted.

Hygroscopic blocking rate:

10 g of water-absorbent resin particles having a particle distribution of 20 mesh or less were placed evenly in an aluminum plate having a diameter of 5 cm. The plate was left in a temperature and humidity controlled chamber at 40° C. and a relative humidity of 80% for three hours. Then the water-absorbent resin particles were sieved with a 12-mesh metal screen, the weight of lumps of the resins which became over 12 mesh by hygroscopic blocking was measured, and the hygroscopic blocking rate was calculated by the following formula.

Hygroscopic blocking rate (%)=(weight of the lumps of the resin particles over 12 mesh)/(total weight of the water-absorbent resin particles after leaving in a temperature and humidity controlled chamber)×100

Dust level:

The inhalation spout of a one-liter suction bottle was connected to a digital dust counter supplied from Shibata Kagaku Co. Ltd. with a glass tube having 7 mm bore and 10 cm length. 20 g of water-absorbent resin particles were dropped into the suction bottle from the mouth thereof by means of a funnel. The number of the dust particles generated from the dropped water-absorbent resin particles per minute was measured with the digital dust counter and the value was defined as the dust level (unit CPM; CPM means count per minute).

Initial absorbency under load and absorption rate:

0.1 g of the water-absorbent resin particles were placed evenly in a cylindrical plastic tube of 30 mm bore and 60 mm height having 250-mesh nylon screen at the botton and a 30 mm diameter weight was placed on the water-absorbent resin particles so that a pressure of 20 g/cm$^2$ is applied thereto.

The plastic tube containing the water-absorbent resin particles was placed in a Petri dish having 12 cm diameter containing 60 ml of physiological saline, with the side having nylon mesh down, and soaked. The increased weight of the water-absorbent resin particles was measured after absorbing the physiological saline for 10 minutes and 60 minutes respectively. The value 10 times as much as the increased weight after 10 minutes was defined as the initial absorbency under load to physiological saline, and the value 10 times as much as the increased weight after 60 minutes was defined as the absorbing capacity under load to physiological saline.

EXAMPLE 1

100 g of water-absorbent resin particles (partially sodium neutralized salt of crosslinked polyacrylic acid) commercially available as "SANWET IM-5000D" from Sanyo Chemical Industries, Ltd. were placed in a plastic bag and 0.2 g of an amino modified silicone oil having the average molecular weight of approximately 20,000 commercially available as "KF-880" from Shin-Etsu Chemical Co., Ltd. was added thereto and mixed thoroughly to obtain the improved water-absorbent resin particles (1) of the present invention. The performance of the resin particles is described in the Table 1.

EXAMPLE 2

100 g of water-absorbent resin particles (surface crosslinked partially sodium neutralized salt of crosslinked polyacrylic acid) commercially available as "SANWET IM-5800" from Sanyo Chemical Industries, Ltd. were placed in a 2,000-ml juicer-mixer and 0.5 g of an epoxy modified silicone oil having the average molecular weight of approximately 9,000 commercially available as "KF-101" from Shin-Etsu Chemical Co., Ltd. was added thereto and mixed thoroughly. The obtained mixture was heated at 150° C. for approximately 20 minutes to obtain the improved water-absorbent resin particles (2) of the present invention.

EXAMPLE 3

100 g of water-absorbent resin particles (partially sodium neutralized salt of crosslinked graft-polymers of starch-acrylic acid salt) commercially available as "SANWET IH-1000" from Sanyo Chemical Industries, Ltd. were placed in a 2,000-ml juicer-mixer and 5 parts of an aqueous solution of methanol which was obtained by dissolving 6 weight % of an epoxy modified silicone oil commercially available as "KF-101" from Shin-Etsu Chemical Co., Ltd. and 2 weight % of ethylene glycol diglycidyl ether commercially available as "Denacol EX-810" from Nagase Kasei Kogyo Co. Ltd. in an 80 weight % aqueous solution of methanol (the ratio corresponds with 0.3 part of "KF-101" and 0.1 part of "EX-810" to 100 parts of water-absorbent resin particles) was added thereto and mixed thoroughly. The obtained mixture was heated at 150° C. for approximately 20 minutes to obtain the improved water-absorbent resin particles (3) of the present invention.

EXAMPLE 4

100 g of commercially available "SANWET IM-1000" particles were placed in a 2,000-ml juicer-mixer and 5 parts of an aqueous solution which was obtained by dissolving 2 weight % of an epoxy modified silicone oil having the average molecular weight of approximately 3,000 commercially available as "X-22-163B" from Shin-Etsu Chemical Co., Ltd. and 6 weight % of polyamine epichlorohydrin resin in 30 weight % aqueous solution of ethylene oxide 3 mole adducts of methanol (the ratio corresponds to 0.1 part of "X-22-163B" and 0.3 part of polyamine epichlorohydrin resin to 100 parts of water-absorbent resin particles) was added thereto and mixed thoroughly. The obtained mixture was heated at 150° C. for approximately 20 minutes to obtain the improved water-absorbent resin particles (4) of the present invention.

Comparative Example 1

The commercially available "SANWET IM-5000D" was used as the water-absorbent resin particles.

Comparative Example 2

The commercially available "SANWET IM-5800" was used as the water-absorbent resin particles.

Comparative Example 3

The commercially available "SANWET IM-1000" was used as the water-absorbent resin particles.

Comparative Example 4

0.5 part of a hydrophobic silica "Aerosil-972" was added to 100 g of commercially available "SANWET IM-5000D" particles to obtain the comparative water-absorbent resin particles (1).

Comparative Example 5

1.0 part of titanium oxide having the particle size of 30 μm was added to 100 g of commercially available "SANWET IM-5000D" particles to obtain the comparative water-absorbent resin particles (2).

Comparative Example 6

5 g of distearyl dimethyl ammonium chloride was melted by heating and was added to 100 g of commercially available "SANWET IM-5800" particles and stirred at 80° C. for 10 minutes. Then 0.5 part of polystyrene particles having the particle size of 20 μm were added thereto to obtain the comparative water-absorbent resin particles (3).

Comparative Example 7

1 g of stearic acid was added to 100 g of commercially available "SANWET IM-5800" particles and heated at 80° C. for 10 minutes to melt the stearic acid with stirring. Then 3 g of silicon oxide was added thereto and mixed thoroughly and cooled to room temperature to obtain the comparative water-absorbent resin particles (4).

Comparative Example 8

100 g of commercially available "SANWET IM-5000D" particles were placed in a plastic bag and 0.5 g of an ordinary silicone oil having an average molecular weight of approximately 6,000 commercially available as "KF-96" from Shin-Etsu Chemical Co., Ltd. was added thereto and mixed thoroughly to obtain the comparative water-absorbent resin particles (5).

The following facts were learned from Table 1.

① The improved water-absorbent resin particles (1)–(4) of the present invention obtained in the Examples 1–4 have dramatically improved hygroscopic blocking rate, dust level, initial absorbency under load and absorbing capacity compared to the untreated water-absorbent resin particles of the Comparative Examples 1–3.

② The improved water-absorbent resin particles (1)–(4) of the present invention obtained in the Examples 1–4 have superior hygroscopic blocking rate, dust level, initial absorbency under load and absorbing capacity compared to the comparative water-absorbent resin particles (1)–(5) obtained in the Comparative Examples 4–8.

Further, although the comparative water-absorbent resin particles (1)–(3) were improved in terms of hygroscopic blocking rate in comparison with the untreated water-absorbent resin particles of the Comparative Examples 1–3, they became inferior in terms of dust level. Moreover, all of the comparative water-absorbent resin particles (1)–(5) became inferior to the untreated water-absorbent resin particles of the Comparative Examples 1–3 in terms of the initial absorbency under load and the absorbing capacity.

TABLE 1

|  |  | hygroscopic blocking rate | dust level | absorbency under load after 10 min | absorbency under load after 60 min |
|---|---|---|---|---|---|
| Example 1 | water-absorbent resin particles (1) of the present invention | 5 | 0 | 26 | 34 |
| Example 2 | water-absorbent resin particles (2) of the present invention | 3 | 2 | 31 | 38 |
| Example 3 | water-absorbent resin particles (3) of the present invention | 1 | 4 | 32 | 37 |
| Example 4 | water-absorbent resin particles (4) of the present invention | 0 | 2 | 31 | 36 |
| Comparative Example 1 | "SANWET IM-5000D" | 95 | 60 | 15 | 30 |
| Comparative Example 2 | "SANWET IM-5800" | 90 | 50 | 24 | 35 |
| Comparative Example 3 | "SANWET IM-1000" | 98 | 70 | 3 | 10 |
| Comparative Example 4 | comparative water-absorbent resin particles (1) | 13 | 210 | 8 | 21 |
| Comparative Example 5 | comparative water-absorbent resin particles (2) | 70 | 980 | 12 | 27 |
| Comparative Example 6 | comparative water-absorbent resin particles (3) | 40 | 80 | 14 | 27 |
| Comparative Example 7 | comparative water-absorbent resin particles (4) | 30 | 40 | 13 | 28 |
| Comparative Example 8 | comparative water-absorbent resin particles (5) | 70 | 5 | 12 | 27 |

EFFECT OF THE INVENTION

The production process of the improved water-absorbent resin particles of the present invention has the following advantages.

① Since the production process of the present invention enables a water-repellent modified silicone oil to be efficiently fixed to the surface of water-absorbent resin particles, it improves the hygroscopic blocking rate in high humidity.

② Since a modified silicone oil is a liquid, unlike other method of adding hydrophobic particles, the dust level may be lowered due to a moistening effect.

③ Since functional groups in the modified silicone oil are reacted with a carboxyl group and/or a carboxylate group in water-absorbent resin particles to improve the hygroscopic blocking rate and crosslink the vicinity of the surface of the water-absorbent resin particles, the initial absorbency under load and absorbing capacity after treatment become improved compared to those of the water-absorbent resin particles before treatment.

④ Since a modified silicone oil is fixed to water-absorbent resin particles by the reaction of the modified silicone oil and a carboxyl group and/or a carboxylate group in the water-absorbent resin particles, only a small amount of the modified silicone oil is needed compared to an ordinary silicone oil to prevent the deterioration of the particle fluidity.

Further, the improved water-absorbent resin particles obtained in the method of the present invention have the following characteristics.

① Since the hygroscopic blocking rate is low, the water-absorbent resin particles do not form blocks and provide good operativity even in the application in high humidity.

② Since the dust level is low, dust is scarcely generated in the process of handling resin particles to provide good operativity and secure the safety of operators without the chance of inhaling the dust.

③ Since the initial absorbency under load and the absorbing capacity are high, when applied to disposable diapers, etc., the water-absorbent resin particles can rapidly absorb much urine, enduring the pressure from the weight of a baby without exuding out the absorbed urine, to provide a good surface dryness of the diapers.

Due to the above-mentioned advantages, the improved water-absorbent resin particles of the present invention obtained by the process of the present invention are useful in various applications such as applications in contact with human bodies including absorbent pads, hygienic materials (disposable diapers for children and adults, sanitary napkins, incontinence pads); applications in contact with food including freshness retaining materials, cooling materials, drip absorbers; applications in materials for separating water from oil, desiccants; applications as water retainers for plants or soil; applications in sludge solidification agents; applications in anti-dewing agents; applications in water blocking materials or packing materials for construction work; and applications in water sealing materials for electric wires or optical fiber cables.

We claim:

1. A process for producing water-absorbent resin particles comprising the step of reacting substantially water-insoluble water-absorbent resin particles with a modified silicone oil, the particles comprising crosslinked polymers of ethylenically unsaturated monomers that comprise acrylic acid and/or acrylic acid salt as an essential element and having an average particle size of 200–600 μm, said modified silicone oil having a functional group capable of reacting with a carboxyl group and/or a carboxylate group in the molecule and having a molecular weight of approximately 1,000–1,000,000 and a viscosity of 10–20,000 cst at 25° C.

2. The process for producing improved water-absorbent resin particles according to claim 1, wherein the modified silicone oil is an amino modified silicone oil and/or an epoxy modified silicone oil.

3. The process for producing improved water-absorbent resin particles according to claim 1, wherein the average molecular weight of the modified silicone oil is 3,000 or more.

4. The process for producing improved water-absorbent resin particles according to claim 1, wherein the weight ratio of the water-absorbent resin particles to the silicone oil is 100:0.001–5.

5. The process for producing improved water-absorbent resin particles according to claim 1, further comprising the step of using a crosslinking agent having at least two functional groups that can react with a carboxyl group and/or a carboxylate group in its molecules at the time of reacting the water-absorbent resins with the modified silicone oil.

6. Improved water-abosorbent resin particles obtained by the process of claim 1, which have a hygroscopic blocking rate of 20% or less under a relative humidity of 80% at 40° C., a dust level of 10 count per minute or less and an absorbing characteristic of initial absorbency under load to physiological saline of 20 times or more.

7. The process for producing improved water-absorbent resin particles according to claim 1, wherein the modified silicone oil is selected from the group consisting of amino modified silicone oil, epoxy modified silicone oil, carbinol modified silicone oil, phenol modified silicone oil and mercapto modified silicone oil.

8. The process for producing improved water-absorbent resin particles according to claim 4, wherein the weight ratio is 100:0.01–3.

9. The process for producing improved water-absorbent resin particles according to claim 4, wherein the weight ratio is 100:0.05–1.

10. The process of claim 1, wherein said particles have a shape selected from the group consisting of spherical, lamellar, block and random shapes.

11. The process of claim 5, wherein said crosslinking agent is selected from the group consisting of polyglycidyl ether compounds, haloepoxy compounds polyaldehyde compounds, polyhydric alcohol compounds and polyamine compounds.

12. The process of claim 5, wherein the weight ratio of the water-absorbent resin to the crosslinking agent is 100:0.01–5.

* * * * *